United States Patent [19]

Kwee et al.

[11] Patent Number: 4,818,517
[45] Date of Patent: Apr. 4, 1989

[54] PHARMACEUTICAL PREPARATION FOR OBTAINING A HIGHLY VISCOSE HYDROGEL OR SUSPENSION

[75] Inventors: Bobby L. S. Kwee, JV OSS; Johannes G. J. Egberink, EB OSS, both of Netherlands

[73] Assignee: Akzo N.V., Arnhem, Netherlands

[21] Appl. No.: 4,714

[22] Filed: Jan. 20, 1987

[30] Foreign Application Priority Data

Jan. 24, 1986 [NL] Netherlands ............... 8600155

[51] Int. Cl.⁴ .............................................. A61K 47/00
[52] U.S. Cl. ..................................... 424/488; 604/36; 424/486
[58] Field of Search ............... 424/19, 22; 604/56, 604/36

[56] References Cited

U.S. PATENT DOCUMENTS 4,178,361 12/1979 Cohen et al. .................. 424/22
4,226,848 10/1980 Nagai et al. ................... 424/19

FOREIGN PATENT DOCUMENTS 2041220 9/1980 United Kingdom .
2147002 5/1985 United Kingdom .

Primary Examiner—Nancy A. B. Swisher
Attorney, Agent, or Firm—William M. Blackstone

[57] ABSTRACT

The invention relates to a pharmaceutical preparation for obtaining a highly viscose hydrogel or highly viscose suspension which is suitable to be introduced by means of an injection syringe into body cavities, and which hydrogel or suspension contains at least a drug, a polymer which is insoluble or sparingly soluble in water but has the capability of swelling in water and a water-soluble thickening agent in a relatively low quantity.

6 Claims, 1 Drawing Sheet

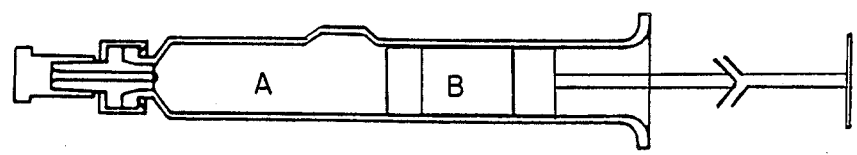

PHARMACEUTICAL PREPARATION FOR OBTAINING A HIGHLY VISCOSE HYDROGEL OR SUSPENSION

The present invention relates to a pharmaceutical preparation for obtaining a highly viscose hydrogel or highly viscose suspension which is suitable to be introduced by means of an injection syringe into body cavities such as the ear, nose, rectum, vagina, uterus and cervix in order to effect a controlled drug release, and which hydrogel or suspension contains at least a drug and a polymer which is insoluble or sparingly soluble in water but has the capability of swelling in water.

A preparation of this type is known inter-alia from the British Patent Specification No. 2,041,220 or U.S. Pat. No. 4,352,790, where a medical preparation is described which promotes the ripening of the cervix and thus facilitates the partus. For this purpose a highly viscose drug containing hydrogen is introduced into the cervical channel. Said hydrogel slowly releases the drug (in this case a prostaglandin) to the neck of the womb, and thus promotes the said ripening of the cervix as a a local effect. The highly viscose prostaglandin-containing gel or suspension referred to in the British Patent Specification is obtained by adding water to a polymer which is insoluble but swellable in water and on which the prostaglandin is adsorbed.

The viscose gel or suspension obtained in this manner is then introduced, preferably with the aid of an injection syringe, in the neck of the womb.

However, the injection, or more generally, the introduction under pressure of a very viscose gel or suspension presents some practical problems.

It turned out in particular that a hydrogel or suspension obtained on the basis of an insoluble but swellable polymer cannot be homogeneously and/or fully "syringed out" presumably because the pressure exerted on the gel or suspension presses water out of the gel or suspension. Depending on the pressure exerted a certain quantity of residue thus remains behind which is no longer syringeable. It is obvious that as a result of such a variable quantity remaining behind, the correct dosaging of the drug is seriously endangered.

It has now been found that a relatively low concentration of a water-soluble thickening agent in the highly viscose hydrogel or suspension can largely improve the syringeability of the original hydrogel or suspension.

The invention therefore provides a pharmaceutical preparation for obtaining a highly viscose hydrogel or suspension, suitable to be introduced into a body-cavity by means of an injection-syringe, said hydrogel or suspension comprising at least a drug and a polymer which is sparingly soluble but swellable in water, and which is characterised in that the preparation also contains a relatively low quantity of a water-soluble thickening agent.

A second embodiment of the invention provides a pharmaceutical preparation in which the quantity of water necessary for the preparation of the highly viscose hydrogel or suspension is already part of the total composition. The latter pharmaceutical preparation comprises (1) a container having two separate compartments, one compartment containing at least dry particles of the polymer which is insoluble or sparingly soluble in water but is swellable and the other compartment containing water, whereby in either or both compartments are additionally present:

(a) a water-soluble thickening agent in a relatively low quantity or concentration;
(b) one or more drugs and optionally
(c) one or more auxiliary substances or carriers usual in pharmacy, and (2) means for bringing the contents of both compartments into contact with each other immediately before use.

The preferred pharmaceutical preparation according to this invention comprises a container having two compartments, one compartment containing the water-soluble but swellable polymer, the drug and one or more auxiliary substances or carriers and the other compartment containing water, the water-soluble thickening agent and one or more auxiliary substances or carriers.

Because the hydrogel or suspension is ultimately to be introduced with the aid of an injection syringe into the body cavity, it is obvious that the most preferred preparation according to the invention is a pharmaceutical preparation in which the said two compartments are already part of an injection syringe (dual compartment syringe).

By the term "drum" is meant, within the scope of the present invention, not only any substance which has a curative action, but all substances which can bring about a biological effect in one manner or another.

In principle all drugs are suitable including drugs which in first instance act systemically. Drugs which are locally (i.e. directly in the respective body cavity) active are however preferred in view of the lower possibility of undesired activities.

An excellent example of locally active drugs is provided by the prostaglandins. The prostaglandins of the E or F type and, in particular, $PGE_2$ and $PGF_{2\alpha}$ are pre-eminently suitable to be used as locally active drugs intended for the inducement or stimulation of the start of the birth.

In addition to said prostaglandins other drugs may be present such as anti-inflammatory and/or bactericidal agents.

Water-insoluble but swellable polymers are usually (internally) crosslinked polymers. Examples of such polymers are mentioned in the already cited British Patent Specification No. 2,041,220, for example crosslinked polymers of starch, dextran, inulin, polyvinyl alcohol, dextrin, sorbitol, etc. Other water-insoluble but swellable polymers are named in the European Patent Application No. 16,654, which polymers can be classified as crosslinked polyethylene oxides.

The swelling capacity of the polymers to be used is not critical, but is in general between 1.5 and 100 ml of water per gram. A swelling capacity of between 2 and 50 ml per gram is to be preferred.

A particular preference is given to those swellable polymers on which the drug is adsorbed already. For a method of preparing such polymers reference is made to the already named British Patent Specification (included herein by reference).

Auxiliary substances, which may be present in the pharmaceutical preparation according to the invention, are for example:

substances capable of rendering the final hydrogel or suspension isotonic, e.g. NaCl, mannitol, sorbitol or dextrose;
moistening agents, (usually surface-active substances) which are able to promote the take-up of water into the swellable polymers;
preservatives; and means to adjust the correct pH of the hydrogel or suspension, e.g. citrate buffers, citric acid, phosphoric acid buffers, etc.

Obviously said auxiliary substances are present in an amount or quantity being effective for the purpose intended.

Water-soluble thickening agents to be used in the present invention can be found in any well-known pharmaceutical text-book. Examples of such water-soluble thickening agents are the readily water-soluble dextrans, cellulose, cellulose derivatives such as hydroxypropylmethylcellulose, methylcellulose, hydroxypropylcellulose, sodium carboxymethylcellulose, and polymers based on acrylic acid such as polyacrylic acid.

In principle, a thickening agent is capable of increasing the viscosity of the solvent if dissolved in said solvent in an effective quantity. However, in the present invention the thickening agent is present in a relatively low quantity or concentration, which means that the thickening agent is present in a quantity which is insufficient per se to significantly rise the viscosity of the quantity of water needed for preparing the hydrogel or suspension. Preferably, the quantity of thickening agent is used in the present invention which is just below the quantity or concentration needed to increase the viscosity of the amount of water necessary for preparing the hydrogel or suspension.

The said quantity cannot be specified in absolute figures in view of the fact that the upper limit is very dependent on the choice of the thickening agent.

Excellent results are obtained with dextran as the water-soluble thickening agent in a quantity of up to approximately 4% by weight referred to the quantity of water necessary to make the final hydrogel or suspension. Preferably, the quantity of dextran is chosen between 2.5 and 3.5% by weight based on the said quantity of water.

A particularly preferred embodiment of the pharmaceutical preparation according to the invention consists of an injection syringe provided with two compartments (as explained previously) which are separated by means of a movable wall, preferably a rubber stopper. Said injection syringe is further provided with a facility for bringing both compartments into contact with each other. For this purpose various embodiments are possible such as a puncturable wall or a wall which can be mechanically removed. A very elegant embodiment is a so-called bypass which is disposed at a suitable point in the injection syringe (see drawing).

EXAMPLES

A. 2 g of prostaglandin $E_2$ is dissolved in a mixture of 850 ml of 96% ethanol and 50 ml of water, after which the solution is filtered through a sterile 0.2 μm membrane filter.

2,000 g of dextrin crosslinked with epichlorohydrin is heated at 160° C. for one hour and then cooled down to ambient temperature. The $PGE_2$ solution is added to the polydextrin and the mixture is mixed for 30 minutes.

The composition thus obtained is subsequently dried under aseptic conditions at 40° C. and reduced pressure.

500.5 mg of this dry material is introduced aseptically into the "needle" compartment of an injection syringe as shown in the drawing. Said compartment (compartment A) thus contains 500 mg of poly-dextrin and 0.5 mg of $PGE_2$.

B. 240 g of dextran 70 (manufacturer: NPBI, the Netherlands) and 72 g of sodium chloride are dissolved in 8,000 ml of water, after which the solution is filtered through a sterile 0.2 μm membrane filter. The solution is then heated in an autoclave for 30 minutes at 121° C. After cooling, 2 ml of this solution are aseptically transferred to the "plunger compartment" of the injection syringe shown in the drawing. Said compartment (compartment B) thus contains 18 mg NaCl, 60 mg of dextran 70 and 2 ml of water.

We claim:

1. Pharmaceutical controlled drug release preparation that, when mixed with water, becomes a highly viscose, homogeneously syringeable hydrogel or suspension, said pharmaceutical preparation comprising at least one drug and at least one polymer, said polymer being insoluble or sparingly soluble in water but having the capability of swelling in water, and further comprising a water-soluble thickening agent, said agent being present in an amount sufficient to prevent separation of water from said hydrogel when being subjected to pressure but less than the amount required to significantly increase the viscosity of the total quantity of water required for swelling the polymer to form the hydrogel or suspension.

2. Pharmaceutical preparation of claim 1, comprising, in addition (1) a container having two separate compartments, wherein one compartment contains a composition comprising dry particles of the polymer that is insoluble or sparingly soluble in water but is swellable in water and the other compartment contains a composition comprising water, and wherein either or both compartments additionally contain:
    (a) the water-soluble thickening agent, and
    (b) one or more drugs, and
    (2) means for bringing the contents of both compartments into contact with each other immediately before use.

3. Preparation according to claim 2, wherein one compartment contains the water-insoluble but swellable polymer, a drug and one or more auxiliary substances or carriers usual in pharmacy and the other compartment contains water, the water-soluble thickening agent and one or more auxiliary substances or carriers usual in pharmacy.

4. Preparation according to claim 3, wherein one compartment contains dry particles of the water-insoluble but swellable polymer having the drug $PGE_2$ adsorbed thereon, and the other compartment contains water, the water-soluble thickening agent and means for making the solution isotonic.

5. Preparation according to claim 1, wherein the water-soluble thickening agent is dextran.

6. Preparation according to claim 5, wherein the quantity of dextran is between 2.5%–3.5% by weight based on the total quantity of water needed for preparing the hydrogel or suspension.

* * * * *